United States Patent [19]
Lussenhop et al.

[11] Patent Number: 5,126,130
[45] Date of Patent: Jun. 30, 1992

[54] MONOCLONAL ANTIBODIES REACTIVE WITH SPECIFIC ANTIGENIC SITES ON HUMAN CYTOMEGALOVIRUS GLYCOPROTEIN A

[75] Inventors: Nancy O. Lussenhop, St. Paul; Bruce E. Kari, Minneapolis; Richard C. Gehrz, Mendota Heights, all of Minn.

[73] Assignee: The Childrens Hospital Incorporated, St. Paul, Minn.

[21] Appl. No.: 83,502

[22] Filed: Aug. 7, 1987

Related U.S. Application Data

[63] Continuation-in-part of Ser. No. 933,789, Nov. 24, 1986, abandoned.

[51] Int. Cl.⁵ ............................................. A61K 39/00
[52] U.S. Cl. ..................................................... 424/85.8
[58] Field of Search ........................................ 424/85.8

[56] References Cited

U.S. PATENT DOCUMENTS 3,959,466  5/1976  Plotkin ................................. 424/89

FOREIGN PATENT DOCUMENTS 180266  7/1986  European Pat. Off. .............. 39/245

OTHER PUBLICATIONS

F. R. Cockerill III, *Mayo Clin. Proc.*, 60, 636 (1985).
Shuster et al., *Mayo Clin. Proc.*, 60, 577 (1985).
Rasmussen et al., *Proc. Nat'l. Acad. Sci. USA*, 81, 876 (1984).
Rasmussen et al., *Journal of Virology*, 55, 274 (1985).
Kim et al., *Journal of Virology*, 20, 604 (1976).
Kim et al., *Journal of Clinical Microbiology*, 18, 331 (1983).
Britt, *Virology*, 135, 369 (1984).
Law et al., *Journal of Medical Virology*, 17, 255 (1985).
L. Pereira et al., *Infection and Immunity*, 36, 924 (1982).
B. Kari et al., *J. Virology*, 60, 345 (Nov. 1986).
W. J. Britt et al., *J. Virol.*, 58, 185 (1986).
G. Farrar et al., *J. Gen. Virol.*, 67, 1469 (1986).
*The EMBO Journal*, vol. 5, No. 11, 1986, IRL Press Limited (Oxford, GB), M. P. Cranage et al.: "Identification of the Human Cytomegalovirus Glycoprotein B. Gene and Induction of Neutralizing Antibodies via its Expression in Recombinant Vaccinia Virus", pp. 3057-3063.

*Primary Examiner*—Frederick E. Waddell
*Assistant Examiner*—T. J. Criares
*Attorney, Agent, or Firm*—Merchant, Gould, Smith, Edell, Welter & Schmidt

[57] ABSTRACT

The present invention is directed to a composition containing a first monoclonal antibody, capable of neutralizing human cytomegalovirus (HCMV), that binds to a first epitope on HCMV GCA, and a second non-neutralizing HCMV monoclonal antibody that binds to a second epitope on HCMV GCA. The GCA complex includes antigenically-related glycoproteins of molecular weights 130,000, 93,000, and 50,000-52,000 kDa. The mixture of the two antibodies has greater neutralizing activity than a composition containing the first antibody alone. Also provided is a method for neutralizing the infectivity of HCMV using the composition.

6 Claims, 3 Drawing Sheets

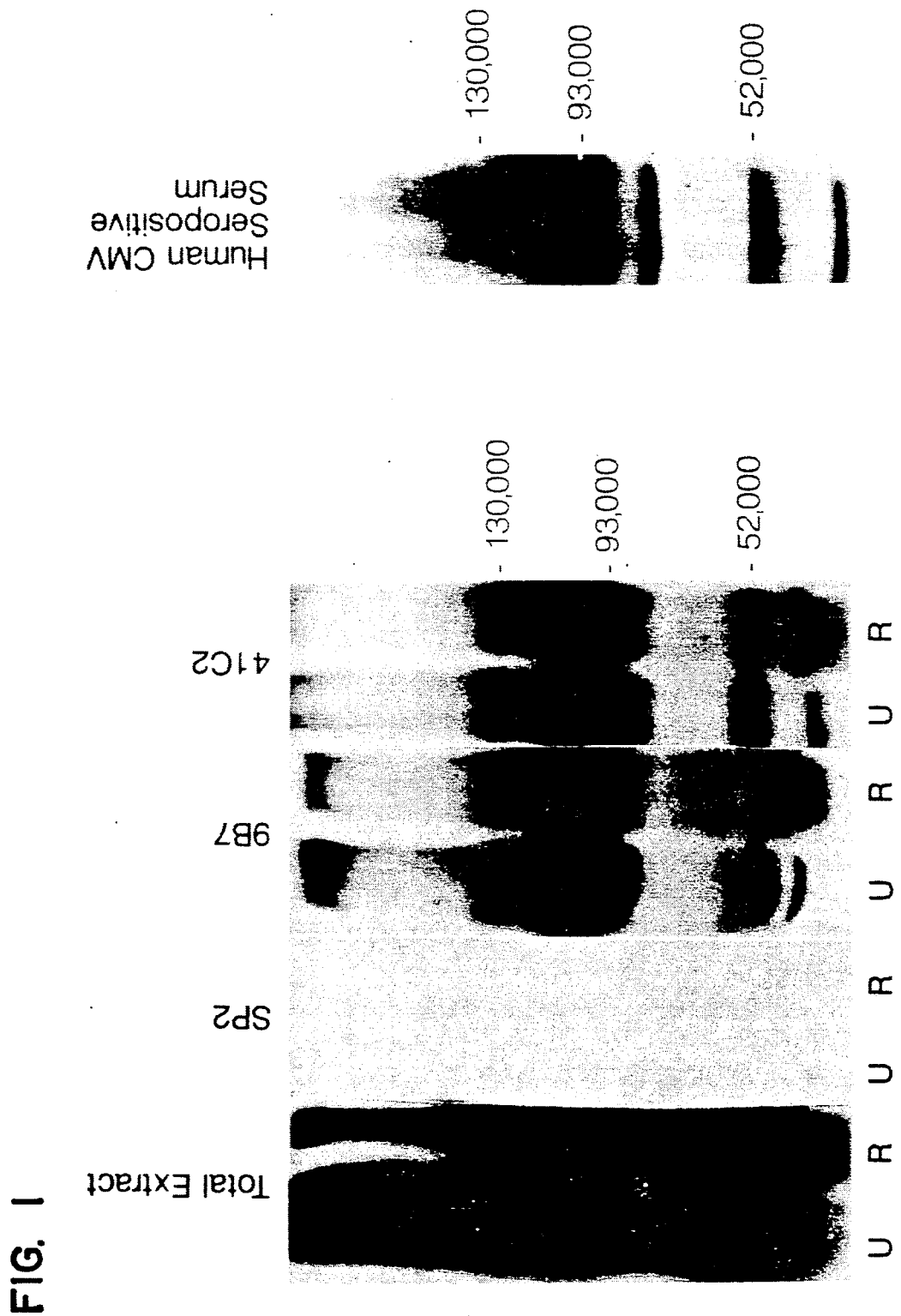

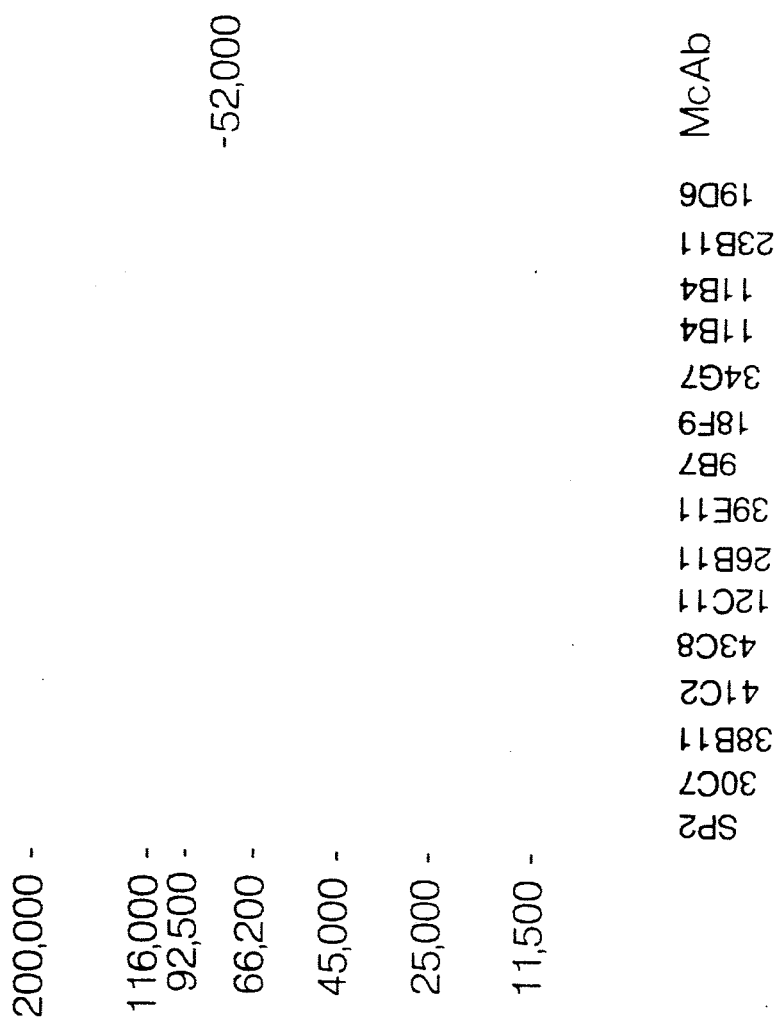

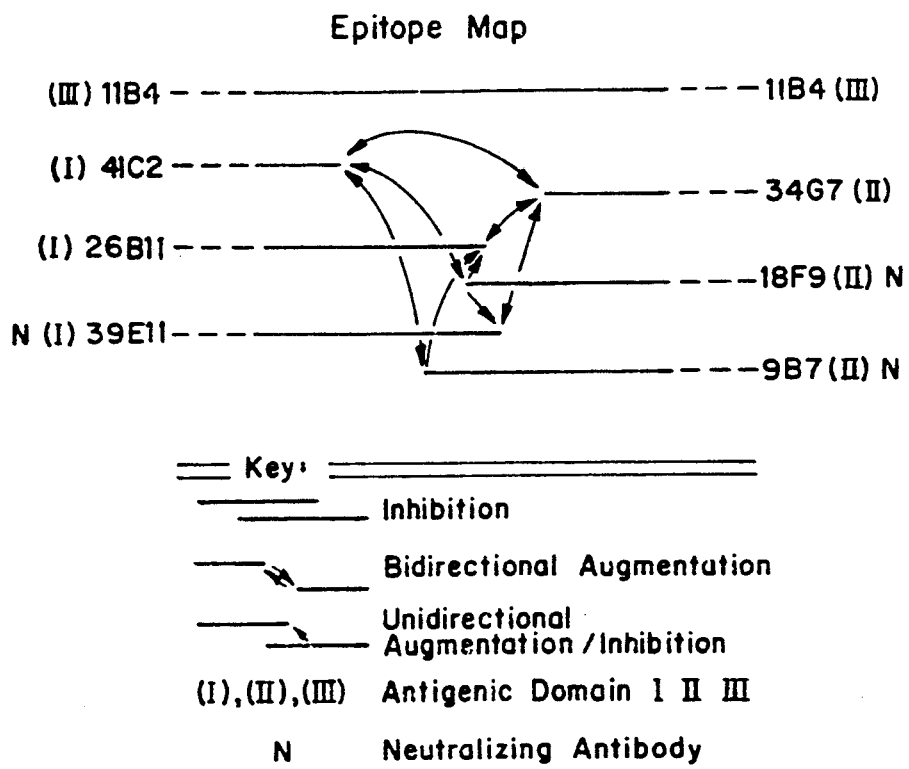
FIG. 3A
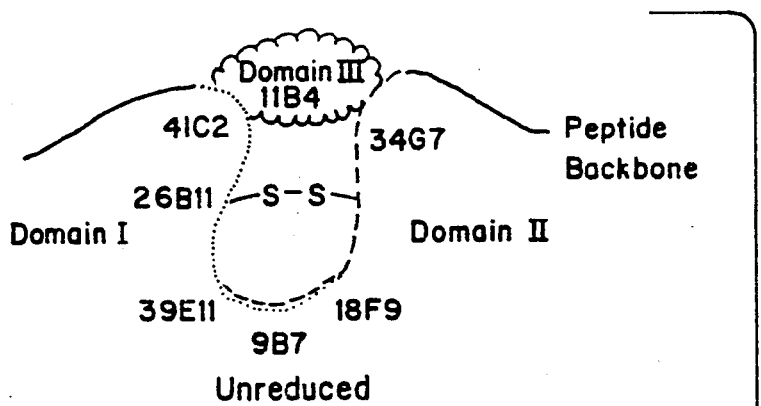
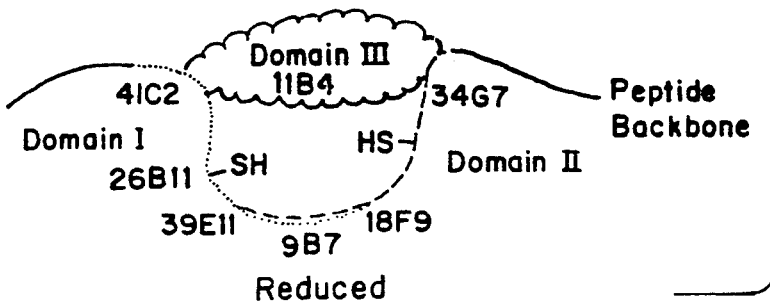
FIG. 3B

MONOCLONAL ANTIBODIES REACTIVE WITH SPECIFIC ANTIGENIC SITES ON HUMAN CYTOMEGALOVIRUS GLYCOPROTEIN A

Government Support

The invention described herein was made with the assistance of the Department of Health and Human Services Grant No. HDMC 5 PO1 HD19937-03 GT. The Government has certain rights in the invention.

CROSS-REFERENCE TO RELATED APPLICATION

This application is a continuation-in-part of U.S. patent application Ser. No. 933,789, filed Nov. 24, 1986, now abandoned.

BACKGROUND OF THE INVENTION

Infection with human cytomegalovirus (HCMV) is usually asymptomatic and self-limiting in the normal human population. However, it can cause serious infection if contracted in utero, leading to severe neurological handicaps and/or deafness in a significant number of cases. Moreover, HCMV is among the most common causes of morbidity and mortality in immunosuppressed patients and patients with immune deficiency diseases.

HCMV is a member of the family herpesvirdae, and is composed of a nuclear complex of nucleic acid and proteins surrounded by an external membrane envelope containing glycopeptides and glycolipids. Among the antigenically distinct envelope (glyco)proteins characterized by our laboratory and others, several are associated by disulfide bonds in high molecular weight complexes. Commonly assigned U.S. patent application Ser. No. 933,789, filed Nov. 24, 1986, entitled, "Immunogenic Glycopeptides of Human Cytomegalovirus" describes the isolation and characterization of antigenically related glycopeptides of molecular weights 93,000 daltons and 50,000-52,000 daltons. These glycoproteins were obtained by the reduction of a set of glycoprotein complexes having molecular weights of ≧450,000 daltons and 130,000-180,000 daltons. Moreover, two prototype murine monoclonal antibodies (mcAb) disclosed in the above patent, 41C2 and 9B7, immunoprecipitate these individual glycoproteins, as well as the antigenically-related glycoprotein complexes. McAb 9B7 also exhibits neutralizing activity against HCMV in vitro in the presence of complement. Convalescent sera from patients who have recovered from HCMV infection also contain antibodies that immunoprecipitate these HCMV glycoproteins, suggesting that antibodies reactive with these glycoproteins may participate in neutralization of virus in vivo.

Therefore, there is a need for HCMV-specific mcAbs that have practical clinical utility in the diagnosis and treatment of HCMV infections. A further needs exists for mcAbs that are useful both in direct detection of HCMV in clinical specimens and rapid identification of the virus in tissue culture. Such antibodies may be used either to capture and concentrate a viral antigen, or alternatively, for immunological detection of the virus using a variety of known immunoassay techniques. There is recent evidence suggesting that the administration of hyperimmune HCMV globulin to immunosuppressed patients prior to organ or bone marrow transplantation may possibly attenuate or prevent life-threatening HCMV infections in the post-transplant period. This same therapy may also be useful in treating patients who already have clinical illness due to HCMV. It is therefore possible that administration of murine mcAbs reactive with individual HCMV (glyco)proteins may also ameliorate the course of HCMV infection in these patients.

BRIEF DESCRIPTION OF THE INVENTION

The present infection provides 13 related murine mcAbs which can be generated by the immunization of mice with whole Towne HCMV virions and/or detergent extracted envelope (glyco)proteins of Towne strain HCMV. The spleen cells of the immunized mice are then fused with a murine myeloma cell line to generate antibody-producing murine B-cell hybridomas. The antibodies produced by these murine hybridomas immunoprecipitate glycoproteins of molecular weights 130,000, 93,000, and 50,000-52,000 daltons. These glycoproteins are associated with one or more high molecular weight glycoprotein complexes in the viral envelope, e.g., in the 130kD glycoprotein complex disclosed in patent Ser. No. 933,789, and referred to herein as human cytomegalovirus glycoprotein A (HCMV GCA).

Competitive enzyme-linked immunosorbent (ELISA) assays were performed to study the relationships among the antigenic sites recognized by the various mcAbs. Surprisingly, either inhibition or augmentation in the binding of the antibodies to the virus was observed when a second antibody was present simultaneously. The mcAbs were assigned to at least 7 groups which recognize distinct antigenic sites within 3 domains of HCMV GCA.

The ability of these mcAbs to neutralize HCMV Towne strain in the presence of complement was tested in a plaque reduction assay. Certain of these mcAbs (i.e., 9E7) were highly neutralizing (2 μg/ml for 50% plaque reduction), whereas other mcAbs (i.e., 41C2) appeared to be non-neutralizing in the presence of complement.

Binding of certain of the neutralizing mcAbs in the ELISA assay was increased two- to four-fold in the presence of a second non-neutralizing antibody. Moreover, the neutralizing activity of the combination of neutralizing and non-neutralizing antibodies was unexpectedly increased by 20-fold compared to that of the neutralizing antibody alone. Even combining two non-neutralizing mcAbs resulted in significant neutralizing activity in certain instances, and such mixtures are also within the scope of the present invention.

Therefore, the present invention is directed to generation of an HCMV-specific murine mcAb produced by a process comprising:
a. immunizing a mouse with a composition comprising HCMV virions or purified HCMV envelope glycopeptides derived from HCMV GCA having molecular weights of about 130,000, 93,000, or 50,000-52,000 daltons; and
b. fusing spleen cells from said mouse with cells from a murine myeloma line to produce hybridomas; and
c. selecting and clonally expanding a hybridoma which produces a mcAb reactive with HCMV GCA glycoproteins of molecular weights 130,000, 93,000, and 50,000-52,000 daltons, but not reactive with herpes simplex, adenovirus or varicella zoster virus.

The mcAbs of the present invention were characterized with respect to their specificity, binding affinity, and their ability to neutralize HCMV in the presence of complement, either alone or in combination with other murine mcAbs of the invention which are also obtained from the hybridomas of step (c) above.

The present invention also provides an effective method for detecting HCMV in a sample of physiological material infected with HCMV. This method comprises:

a. reacting said physiological material with a first monoclonal antibody which binds to a first epitope of HCMV GCA to form a complex between said HCMV GCA and said first monoclonal antibody; and b. reacting said complex with a second monoclonal antibody to a second epitope of HCMV GPA, wherein the second monoclonal antibody enhances the binding of the first monoclonal antibody to the first epitope, and wherein said second monoclonal antibody comprises a detectable label or a binding site for said label, to yield a ternary complex; and c. detecting the presence of said label, or alternatively, reacting said binding site with a detectable label prior to said detection. The concentration of said label provides a measure of the concentration of HCMV GCA present in said physiological material.

Preferably, the detectable label is a radioactive isotope or an enzyme which has been chemically linked to the second antibody. Preferably, the binding site for said label is provided by a molecule capable of binding a free enzyme or a radioisotope, e.g., biotin or deferoxamine. These molecules can be chemically linked to mcAbs by methods known to the art. For example, see U.S. Pat. No. 4,680,338. The enzyme preferably is linked to a substance which binds strongly to the binding site, for example, an avidinenzyme conjugate will bind to biotin. Steps (a) and (b) can be performed simultaneously or the order of addition of the first and second mcAb can be inverted.

The ability to neutralize HCMV infectivity in vitro with a composition which contains a high titer of monoclonal antibodies to HCMV GCA can provide the basis for assays of the effectiveness of some prototype HCMV vaccines, and will also be useful in basis investigations into the mechanisms of HCMV infection, e.g., with respect to the effect of mutations on the products of viral gene expression.

The present invention is also directed to a method for raising plasma immunogenicity to HCMV GCA by administering a pharmaceutical unit dosage form comprising one or more of the present antibodies to a patient who has been exposed to HCMV. Therefore, it is believed that the antibodies of the present invention will have therapeutic potential, either as a prophylactic agent to prolong the life expectancy of infected and/or diseased patients by retarding the clinical progression of the disease, or possibly, as a curative agent which can act to eliminate the virulence of the virus. The present antibodies might also represent a valuable adjunct to chemical antiviral agents.

The isolated mcAbs preferably are diluted with a pharmaceutically-acceptable liquid carrier, such as an aqueous IV fluid, prior to being assayed for bioactivity or administered as a unit dosage form in vivo. See Remington's *Pharmaceutical Sciences*, A. Osol, ed., Mack Pub. Co., Easton, PA (16th ed. 1980) at pages 1488-1496, the disclosure of which is incorporated by reference herein. The resultant solution is sterilized, e.g., by filtration. Preservatives commonly employed with IgG preparations, such as maltose, glycine or thimerosal, may be added in pharmaceuticallyacceptable amounts.

The resulting solutions are preferably administered parenterally, e.g., by intravenous infusion or injection. The amount of mcAb composition administered will vary widely, and will depend on the physique and physical condition of the HCMV-infected patient. Such factors are necessarily empirical, and can be determined by the clinician, employing known HCMV staging criteria. In some clinical situations, it may be necessary to administer a plurality of doses of the mcAb composition, in order to neutralize the infectivity of viral particles as they are released from infected target cells.

BRIEF DESCRIPTION OF THE DRAWINGS

FIG. 1 is an SDS-PAGE separation of HCMV-GCA glycoproteins (unreduced and reduced) that were immunoprecipited by GCA-specific monoclonal antibodies 9B7 and 41C 2 (SP2 =control monoclonal antibody), and SDS-PAGE separation of glycoproteins immunoprecipitated by Human CMV positive convalescent sera. (U=unreduced extract material; R=reduced extract material.)

FIG. 2 is a Western Blot of HCMV glycoproteins recognized by GCA-specific monoclonal antibodies.

FIG. 3A is an epitope map of antigenic sites recognized by monoclonal antibodies in three domains on HCMV GCA.

FIG. 3B is a hypothetical model of the location of epitopes in three domains on HCMV GCA.

DETAILED DESCRIPTION OF THE INVENTION

Materials and Methods

A. Preparation of Viruses

HCMV Towne strain and AD169 strain were grown with or without $^3$H-glucosamine on human skin fibroblast cultures, harvested and purified on sucrose gradients as described previously (Kari et al., J. Virol., 60, 345-352 (1986)). The purified virus was resuspended in Tris-NaCl buffer (50 mM Tris hydrochloride, 150 mM NaCl pH 7.4), and extracted with 1% Nonidet P-40 (NP-40, Sigma Chem. Co., St. Louis, MO) in Tris-NaCl buffer (50 mM Tris hydrochloride, 10 mM NaCl, 2 mM phenylmethyl sulfonylfluoride pH 7.5) as described by Kari et al., in J. Virol., 60, 45-52 (1986). Uninfected skin fibroblasts were extracted in a similar fashion for use as negative controls. Reduction and alkylation of HCMV Towne NP-40 crude extracted material was performed as described by Kari et al., J. Virol., 60, 345-352 (1986). All detergent extracted viral or control fibroblast materials were passed over an Extracti-Gel D column and eluted with water to remove the detergent.

B. Generation of Murine Monoclonal Antibodies to HCMV

The production of mouse hybridomas secreting mcAbs to HCMV proteins was performed as previously described (Kari et al., J. Virol., 60, 345-352 (1986)). The antibodies described in this patent application involved three separate fusion experiments using either AD169 or Towne strain purified HCMV virions. Balb/C mice were immunized for 2, 5 or 10 months. Spleen cells from immunized mice were fused with SP2-2-Ag14 myeloma cells (American Tissue Culture Collection) using polyethylene glycol as the fusing agent.

Resulting hybrid cells were screened for specific antibody production to HCMV using an enzyme-linked immunosorbent assay (ELISA). (See Section G below.) Antigens used in the ELISA assay were either purified HCMV Towne Strain or AD169 strain whole virions or HCMV Towne NP-40 extracted material or NP-40 extracted material from uninfected skin fibroblasts. Ascites fluids from expanded clones were purified for IgG using high performance hydroxyapatite chromatography (HPLC) (JuarezSalinas et al., Biotechniques, 2, 164 (1984)). The titer of fractions collected from the column was measured with respect to HCMV-specific activity using the ELISA assay. The protein content of the fractions was determined using the BioRad protein assay (BioRad) and purified mouse IgG as a standard. Only fractions with the highest titers from each run were used for subsequent experiments. The hybridomas 41C2 and 9B7 consistently produce 5-10 mg of monoclonal antibody per 1 ml of ascites.

The clonality of the mcAbs was established by twice subcloning of the hybridomas producing each antibody. Furthermore, each antibody had a unique isotype (i.e., 41C2-IgG1; 9B7 IgG-2b), and each appears as an individual antibody by isoelectric focusing.

C. Immunoprecipitation

Monoclonal antibodies were allowed to immunoprecipitate $^3$H-glucosamine-labelled HCMV Towne NP-40 extracted proteins which were unreduced or reduced and alkylated prior to immunoprecipitation. Proteins were solubilized in sodium dodecyl sulfate (SDS) and separated by SDS polyacrylamide gel electrophoresis. The tritium-labelled glycoprotein bands in the gel were indentified by fluorography as described (Kari et al., J. Virol., 60, 345-352 (1986)).

D. Western Blot

For Western Blot assays, purified HCMV Towne strain whole virus was solubilized with SDS and separated by 5-15% gradient polyacrylamide gel electrophoresis. The proteins on the gel were subsequently electroblotted onto nitrocellulose paper with a BioRad transblot apparatus. The paper was blocked with 3% gelatin in Tris buffered saline (TBS, 20 mM Tris, 500 mM NaCl pH 7.5). The mcAbs in ascites fluid were diluted 1/500 in 1% gelatin in TBS, and allowed to bind to the paper overnight at room temperature. The paper was washed with PBS-0.05% Tween 20 (polysorbate 20), and alkaline phosphatase-labelled goat anti-mouse IgG (KPL) diluted 1/2000 with 1% gelatin in TBS was added and allowed to incubate for one hour at room temperature. The paper was washed once again and the substrate 5-bromo-4-chloro-3-indolylphosphate/niброblue tetrazolium in 0.1M Tris buffer solution (KPL) was added. Reaction of the antigen-antibody complex with the substrate resulted in the formation of an insoluble purple product. The reaction was stopped by immersing the paper in water.

E. Simultaneous Two Antibody Binding Assay

HCMV antigens were coated onto 96 well microtiter Immulon II plates by incubating 200 ng of total protein in 50 μl of 0.05M carbonate buffer (pH 9.5) per well for 18 hours at 4° C. The wells were then washed three times with phosphate-buffered saline with 0.05% Tween 20 (PBST), once with distilled water, and then were air dried. The plates were stored at 4° C. with dessicant until use. The antigens used included purified HCMV Towne strain whole virion, unreduced and reduced proteins extracted from skin fibroblasts infected with HCMV Towne strain for 8-12 days (See Section A, preparation of viruses), or NP-40 extracted proteins derived from uninfected skin fibroblasts (See Section A, preparation of viruses).

The mcAbs in ascites fluids were purified by HPLC and biotinylated using biotin N-hydroxysuccinimide ester. Twenty-five μl of a fixed amount of biotinylated antibody and 25 μl of PBST or 25 μl containing varying amounts (50 μg to 10 pg) of a second unlabelled mcAb were added simultaneously to the antigen-coated wells and incubated for 90 minutes at room temperature. The wells were washed 3 times with PBST and 50 μl/well of peroxidase-labelled streptavidin (KPL) diluted 1/2000 in PBST was added and the mixture incubated for 90 minutes at room temperature. After washing 3 times with PBST, the substrate o-phenylenediamine (OPD) and $H_2O_2$ in citrate buffer as added and the reaction was stopped after 15 minutes with 2.5N $H_2SO_4$. Optical denisty (O.D.) of the product was read with a Dynatech plate reader at 490 nm. The biotinylated antibody was titered in 10-fold dilutions beforehand to determine the amount that would give an O.D. of >0.5 and <1.5 in the absence of a second antibody.

The unlabelled second antibody was shown to be active by titering against HCMV whole virus antigen. The amount of binding was quantitated by adding peroxidase-labelled goat antimouse IgG and the substrate OPD. The assay was performed in duplicates and the data were compiled using the following formula:

Percent of augmentation or inhibition =

$$\frac{(OD^{490} \text{ in presence of 2nd antibody}) - (OD^{490} \text{ in absence of 2nd antibody})}{(OD^{490} \text{ in absence of 2nd antibody})} \times 100$$

F. Neutralization Plaque Reduction Assay

Monoclonal antibodies purified by HPLC and titered positive against Towne strain virus in an ELISA assay (Section B, above) were tested for neutralizing activity aainst the same virus in a plaque reduction assay as described by Kari et al., supra. About 1,000-2,000 PFU of Towne strain virus were added to a single antibody at a protein content of 100 μg to 0.001 μg along with 2% guinea pig complement (Pel-Freez Biologicals, Rogers, AK) in a total volume of 0.05 μl of Dulbecco Modified Eagle Medium (DMEM). When two antibodies were used, an additional 10-20 μg/μl of the second antibody was added to the test sample. Virus neutralization was expressed as % plaque reduction using the formula:

Percent plaque reduction =

$$\frac{(\text{Average } PFU \text{ with no antibody}) - (\text{Average } PFU \text{ with antibody})}{(\text{Average } PFU \text{ with no antibody})} \times 100$$

G. ELISA Detection of HCMV in Supernatants of Tissue Cultures Inoculated with Clinical Specimens Monolayers of human skin fibroblasts in either 24 well plates or shell vials are inoculated with clinical specimens (urine or saliva) obtained from patients suspected to have HCMV infection. Uninoculated skin fibroblasts are processed in the same fashion as a negative control.

Five days after inoculation, the tissue culture media fluid is removed from the fibroblast monolayer by vacuum suction. Two hundred μl phosphate buffered saline (PBS) are added to each well and completely removed by suction. One hundred μl of solubilizing PBS-1% NP-40 are added to each well for five minutes. The bottom of each well is then scraped with a pipette and cells are resuspended thoroughly by repeated pipetting. This suspension of lysed cells is employed as the "patient sample" in Section H, below.

H. ELISA Assay for Detection of HCMV in Tissue Culture Supernatants

Microtiter wells in 96-well microtiter plates are precoated with HCMV GCA-specific mcAb 41C2 (IVI-10119) as the capture antibody. Included in each plate are a blank well, a well for an uninfected fibroblast control and an HCMV positive control well in addition to wells for patient samples. After coating with the capture antibody, the microtiter wells are washed once with buffer (PBS-0.05% Tween). Sample solutions are solubilized in PBS-1% NP-40 in each tissue culture well, and are then dispensed into individual microtiter wells. Blank, negative skin fibroblast and HCMV positive control samples are included with each clinical sample determination.

Five μl of biotinylated GCA-specific mcAb 9B7 (IVI-10117), which recognizes a different epitope on GCA than that recognized by 41C2, are then added to each microtiter well as a detection antibody. The microtiter plate is then placed in a plastic bag and incubated at 37° C. for 1 hour. Wells are then washed 4 times with wash buffer (PBS-0.05% Tween), 100 μl of streptavidin-peroxidase is added and the plate is incubated for 30 minutes at 37° C. in a plastic bag. Wells are then washed 4 times with wash buffer and then one time with distilled water. Ortho-pheylenediamine (OPD) substrate (100 μl) is added and reacted for 15 minutes at room temperature. The reaction is then stopped with 25 μl of 5N $H_2SO_4$. After 10 minutes, the microtiter plate is read with a Dynatech plate reader at 490 nm or by visual colorometric reading. This method has been shown to detect HCMV at a total protein concentration of 10 nanograms.

Results

A. Immunoprecipitation of HCMV Envelope Glycoproteins by Murine Monoclonal Antibodies 1. Methodology Purified $^3$H-glucosamine-labelled HCMV Towne strain virions were extracted with 1% NP-40. The unreduced material, or material reduced with dithiothreitol and alkylated with diiodoacetamide, was immunoprecipitated with 13 murine mcAbs. After immunoprecipitation, all samples were further reduced with β-mercaptoethanol and separated by SDS-PAGE. Fluorography showed that all the mcAbs precipitated antigenically related glycoproteins with molecular weights of 130,000, 93,000, and 50,000–52,000 daltons, whether or not the extract had been reduced prior to immunoprecipitation (Representative results are shown in FIG. 1, where SP2=control mcAb.).

Thus, the number and relative amounts of the individual proteins immunoprecipitated were not affected by reduction prior to immunoprecipitation. Minor variations in the molecular weights of the species of glycoproteins precipitated between 50–52,000 may reflect slight differences in charge and/or conformation following immunoprecipitation with mcAbs recognizing different epitopes on the same glycoproteins. The mcabs also recognized the 52,000 dalton glycoprotein of HCMV GCA by Western Blot, whereas the higher molecular weight species were not consistently identified by this method (Representative results are shown in FIG. 2).

2. Discussion

We have isolated 2 antigenically related high molecular weight glycoprotein complexes having molecular weights of (a) more than 450,000 daltons and (b) 130,000–180,000 daltons, from the envelopes of HCMV virions by anion-exchange HPLC, which we have designated as HCMV GCA. Upon reduction of disulfide bonds, individual glycoproteins of molecular weights 130,000, 93,000, and 50,000–52,000 daltons were identified. As shown in FIG. 1, all three constituent glycoproteins, as well as the disulfide-linked complexes, could be immunoprecipitated by the prototype mcAbs 41C2 and 9B7, suggesting that these antibodies recognize a unique class of HCMV envelope glycoproteins and glycoprotein complexes. Human HCMV positive convalescent sera also immunoprecipitated glycoproteins similar to those recognized by these mcAbs. The immunoprecipitation pattern recognized by the prototype mcAbs 41C2 and 9B7 using HPLC purified glycoproteins comprising the HCMV GCA complex identified the major glycoprotein A-(gA) intermediate of 130,000 daltons as well as the two mature A-type glycoproteins of 93,000 and 50,000–52,000 daltons.

Monoclonal antibodies 41C2, 9B7 and 11 additional mcAbs have been shown to immunoprecipitate the same three glycoproteins from detergent extracts of HCMV virions. The presence of the precursor glycoprotein reflects contamination of virion preparations with cell-associated viral glycoprotein intermediates that result from the method used to obtain large quantities of HCMV for these studies. Although we have shown that HCMV contains additional glycoproteins of similar molecular weights to those comprising GCA, the pattern of 3 antigenically related glycoproteins recognized by the mcAbs described herein is unique to GCA and thus it can be concluded that all 13 monoclonals recognize the same glycoprotein complex, GCA.

B. Simultaneous Binding of Two Monoclonal Antibodies to HCMV Glycoproteins Expressed on the Surface of Purified Towne Strain HCMV As shown in FIGS. 1 and 2, thirteen murine mcAbs were identified to be specific for the antigenically-related 130,000, 93,000 and 50,000–52,000 dalton envelope glycoproteins of HCMV based on immunoprecipitation and Western Blot data. All mcAbs were IgG-purified by hydroxyapatite HPLC and concentrated to the desired protein content using a multi-micro ultrafiltration system (Amicon) equipped with a YM10 filter. The envelope glycoproteins were presented as antigen on whole virions adsorbed onto 96 well microtiter polystyrene plates.

Competitive enzyme-linked immunosorbent (ELISA) assays were performed in order to study the relationships among the antigenic sites recognized by the various antibodies. In our initial studies, fixed amounts of biotinylated and unlabelled mcAbs were added simultaneously to determine the relative inhibition or augmentation of binding of the labelled antibody to the virus in the presence of the second unlabelled antibody. All thirteen mcAbs were tested for competitive binding with two neutralizing (9B7, 18F9) and two non-neutralizing (41C2, 34G7) biotinylated antibodies. As demonstrated by the data summarized on Table 1, below, the mcAbs exhibited 4 distinct patterns based on their ability to inhibit or augment binding of other mcAbs belonging to the same or different groups.

4. Monoclonal antibodies 11B4 and 23B11 inhibited the binding of all four biotinylated mcAbs.
5. Monoclonal antibody 19D6 inhibited the binding of biotinylated 41C2 and had little or no effect on the binding of biotinylated 9B7, 34G7 and 18F9.

There was no correlation between the pattern of inhibition or augmentation of binding of the mcAbs with their neutralizing activity.

Moreover, it was not possible from these data to construct a definitive epitope map, since the inhibition or augmentation of binding of any particular mcAb in combination with other mcAbs was likely to be depen-

TABLE 1

INHIBITION/AUGMENTATION OF BINDING OF A FIXED AMOUNT OF BIOTINYLATED McAb BY A FIXED AMOUNT OF UNLABELLED McAb

| | Unlabelled Antibody | IgG Subtype | Neutralizing Activity | Percentage of Inhibition (−) Augmentation (+) | | | |
|---|---|---|---|---|---|---|---|
| | | | | Biotinylated 41C2 | Biotinylated 34G7 | Biotinylated 9B7 | Biotinylated 18F9 |
| | 15 μg | | | 12.5 ng. | 5 ng. | 25 ng. | 25 ng. |
| | 12C11 | $G_{2a}$ | ND | −81 | +8 | −95 | −93 |
| I | 39E11 | $G_{2a}$ | Yes | −90 | −3 | −91 | −94 |
| I | 26B11 | $G_{2b}$ | No | −96 | +34 | −73 | −68 |
| I | 41C2 | $G_1$ | No | −99 | +39 | +306 | +153 |
| | 30C7 | $G_1$ | ND | −91 | +17 | +209 | +105 |
| | 38B11 | $G_1$ | ND | −98 | +12 | +143 | +97 |
| | 43C8 | $G_1$ | ND | −97 | +30 | +208 | +119 |
| II | 9B7 | $G_{2b}$ | Yes | −13 | −69 | −81 | −97 |
| II | 18F9 | $G_{2b}$ | Yes | +78 | −88 | −80 | −97 |
| II | 34G7 | $G_{2a}$ | No | +30 | −93 | −81 | −96 |
| III | 11B4 | $G_{2b}$ | No | −65 | −73 | −88 | −86 |
| | 23B11 | $G_1$ | ND | −72 | −42 | −16 | −24 |
| | 19D6 | $G_1$ | ND | −37 | +7 | −10 | −1 |

ND = not done
Values given are averages from two experiments with duplicates run in each experiment.

The following results were observed:
1. Monoclonal antibodies 12C11, 39E11 and 26B11 inhibited binding of biotinylated 41C2, 9B7 and 18F9, but had little or no effect on the binding of biotinylated 34G7 (IVI-10142).
2. Monoclonal antibodies 41C2, 30C7, 38B11 and 43C8 inhibited the binding of biotinylated 41C2 and augmented binding of the other 3 biotinylated mcAbs (34G7, 9B7, 18F9).
3. Monoclonal antibodies 9B7, 18F9 and 34G7 inhibited the binding of biotinylated 34G7, 9B7 and 18F9, whereas these same mcAbs either augmented or did not affect the binding of biotinylated 41C2.

dent upon the binding affinity of each antibody at the particular protein concentration used for these initial studies.

Therefore, topographical analysis of the antigenic sites recognized by 7 of these mcAbs was characterized in greater detail by adding varying amounts of unlabelled mcAb to the same or different biotinylated mcAbs to determine the extent of inhibition and/or augmentation of binding. the simultaneous binding of all combinations of unlabelled and biotinylated mcAbs 26B11, 39E11, 34G7, 11B4, 18F9, 17B8, 41C2 and 9B7 to whole virus was studied, and the results are summarized on Table 2, below.

TABLE 2

MAXIMAL INHIBITION/AUGMENTATION OF BINDING OF FIXED AMOUNT OF BIOTINYLATED McAb BY SIMULTANEOUS ADDITION OF VARYING AMOUNTS OF UNLABELLED McAb

| Unlabelled McAb | Biotinylated McAbs | | | | | | |
|---|---|---|---|---|---|---|---|
| | Group I | | | Group II | | | Group III |
| | 41C2 | 26B11 | 39E11 | 34G7 | 18F9 | 9B7 | 11B4 |
| Group I | | | | | | | |
| 41C2 | −88% | −93% | −89% | +73 | +89% | +195% | −53% |
| 26B11 | −93% | −95% | −92% | +93 | −44% | −54% | −70% |
| 39E11 | −86% | −97% | −95% | +49 | −90% | −89% | −64% |
| Group II | | | | | | | |
| 34G7 | +96% | +98% | +55% | −80% | −85% | −75% | −78% |
| 18F9 | +130% | +77% | +105% | −77% | −93% | −90% | −70% |
| 9B7 | +48% | −21% | +2% | −86% | −95% | −86% | −66% |
| Group III | | | | | | | |
| 11B4 | −52% | −24% | −33% | −68% | −55% | −57% | −54% |
| Unrelated McAb | | | | | | | |
| 17B8 | −13% | −5% | −9% | −13 | −7% | −14% | −18% |

As can be seen from the data summarized on Table 2, addition of increasing amounts of unlabelled mcAb inhibited the binding of the same biotinylated antibody by 80% or more with the exception of 11B4, which inhibited the homologous biotinylated antibody to maximum of 54%. Adding increasing amounts of mcAb 17B8, which recognizes an unrelated non-glycosylated HCMV protein of molecular weight 24,000 daltons in Western Blot but does not immunoprecipitate and $^3$H-glucosamine labelled material, did not significantly affect the binding of any of the biotinylated GCA-specific antibodies. Thus, the inhibition and/or augmentation observed among the various combinations of GCA-specific mcAbs involves direct competition for the antigenic sites expressed on the GCA glycoproteins, rather than being due to the non-specific interaction of immunoglobulin molecules.

Based on the inhibition/augmentation curves generated for all possible combinations of pairs of the 7 mcAbs, it was possible to classify the antibodies into three major groups (Table 2). Group I consisted of antibodies 41C2, 26B11 and 39E11, and was constituted on the basis of the ability of each mcAb within this group to mutually inhibit binding of other mcAbs within the group to their specific antigenic sites. Similarly, group II, comprising antibodies 34G7, 18F9 and 9B7, exhibited mutual inhibition among all antibodies within this group. Group III consisted of a single, unique mcAb 11B4, which inhibited the binding of all of the other GCA-specific antibodies in groups I and II, and was itself inhibited in the presence of all of the other mcAbs.

Although individual mcAbs within the three major groups exhibited similar inhibitory patterns, significant differences were observed in their capacity to augment binding of mcAbs in unrelated groups. Antibody 41C2 in group I augmented the binding of antibodies 34G7, 18F9 and 9B7 in group II. Moreover, group II antibodies augmented the binding of biotinylated 41C2. This mutual augmentation of binding was also observed between mcAb 34G7 in group II and antibodies 41C2, 26B11 and 39E11 in group I. Both 26B11 and 39E11 in group I inhibited the binding of 18F9 and 9B7 in group II. However, 18F9 augmented the binding of 26B11 and 39E11 while 9B7 enhanced the binding of 26B11 but not 39E11.

Inhibition of binding of the biotinylated mcAb was dependent on the protein concentration of the competing, unlabelled mcAb, and often reached a maximum which was maintained at higher concentrations of unlabelled antibody. Augmentation between two antibodies occurred in the presence of optimal concentrations of unlabelled antibody, whereas further increases in the concentration of the enhancing antibody resulting in no further enhancement and in some cases resulted in a decrease in augmentation or inhibition of binding of the biotinylated antibody.

C. Simultaneous Binding of Two Antibodies to Viral Glycoproteins in Unreduced and Reduced Detergent-Extracted Material from HCMV Towne Strain Since the antigenic glycoproteins recognized by these mcAbs are normally present in the virus as glycoprotein complexes linked by disulfide bonds, similar competitive binding assays were performed using reduced or unreduced detergent-extracted material to determine the role of conformational structure in the binding of specific mcAbs to their respective epitopes. Antibodies 41C2 and 39E11 in group I and antibodies 9B7 and 34G7 in group Ii were tested. These pairs of antibodies continued to mutually inhibit binding of other antibodies within the same group to GCA that had been extracted from whole virus, or to individual gA glycoproteins obtained by reduction and alkylation of detergent extract to prevent re-association of disulfide bonds.

Competitive binding between mcAb 41C2 (group I) and 9B7 (group II) and between antibodies 41C2 (group I) and 34G7 (group II) was then re-examined using unreduced or reduced detergent extracts of HCMV virions. When the antigen recognized was in the form of unreduced extracted material, the ability of 9B7 and 34G7 to enhance binding of 41C2 to its epitope was diminished compared to whole virus. When reduced material was tested, 9B7 and 34G7 no longer augmented binding of 41C2. Conversely, 41C2 continued to augment the binding of 9B7 to unreduced extracted material to the same extent as that to whole virus, whereas disruption of disulfide linkages by reduction dramatically reduced this augmentation. The enhancing effect of 41C2 on the binding of 34G7 to GCA in unreduced and reduced virus extracts was very much diminished compared to that in whole virus.

Antibody 18F9 (group II) enhanced the binding of 39E11 and 26B11 to GCA on the whole virus, whereas 39E11 and 26B11 reciprocally inhibited the binding of 18F9. When the reactivities of these antibodies were re-examined using unreduced extracted material, 18F9 was noted to inhibit the binding of 39E11 and 26B11, while 39E11 and 26B11 continued to inhibit the binding of 18F9. With reduced material, they mutually inhibited each other except for 26B11, which had virtually no effect on the binding of 18F9. The antibody 11B4 (group III) continued to mutually inhibit the binding of all other mcAbs, whether HCMV GCA or gA was recognized on whole virus or in reduced or unreduced viral extracts.

Thus, it was apparent that the ability of certain mcAbs to augment binding of certain other mcAbs to unreduced detergent extract of HCMV was diminished compared to their ability to augment binding of the same mcAbs to nascent virus in many cases. Furthermore, reduction of disulfide bonds markedly diminished the augmenting effect of these mcAbs in most cases, suggesting that the conformational structure of the GCA glycoprotein complexes played a significant role in the augmentation of binding.

D. Synergistic Neutralizing Activity of Mono-Clonal Antibodies

The biological significance of cooperative binding between mcAbs seen in the ELISA assay was demonstrated by examining their neutralizing activity agains HCMV Towne strain. The neutralizing activity of individual mcAbs was first determined in the presence or absence of complement at IgG protein concentrations of 0.001-100 µg/well. Greater than 50% plaque reduction was considered to be consistent with specific neutralizing activity against Towne strain HCMV. The results of these assays are summarized in Table 3, below.

TABLE 3
NEUTRALIZING ACTIVITY OF INDIVIDUAL McAbs IN THE PRESENCE OF COMPLEMENT

| Group | McAb | Neutralizing Activity | Protein Concentration to Achieve ≧50% Plaque Reduction |
|---|---|---|---|
| I | 41C2 | — | non-neutralizing |
|   | 26B11 | ± | 6.5 μg/well |
|   | 39E11 | + | 0.5 μg/well |
| II | 34G7 | — | 50 μg/well* |
|   | 18F9 | + | 5 μg/well |
|   | 9B7 | + | .55 μg/well |
| III | 11B4 | — | non-neutralizing |

*At ≧50 μg/well, neutralizing activity may reflect non-specific effect of high IgG concentration.

Group I mcAb 41C2 did not exhibit neutralizing activity at any protein concentration, whereas 26B11 and 39E11 neutralized HCMV at protein concentrations of 6.5 μg/well and 0.5 μg/well, respectively. Among group II mcAbs, 34G7 was non-neutralizing; 9B7 and 18F9 both neutralized HCMV in the presence of complement at concentrations of 0.55 μg/well and 5 μg/well, respectively. The group III mcAb 11B4 did not neutralize Towne HCMV.

Three pairs of mcAbs were tested for synergistic neutralizing activity against Towne strain HCMV. The results of these tests are summarized on Table 4, below.

TABLE 4
SYNERGISTIC NEUTRALIZING ACTIVITY USING COMBINATIONS OF NEUTRALIZING AND NON-NEUTRALIZING McAbs IN THE PRESENCE OF COMPLEMENT

| McAb(s) | *PROTEIN CONCENTRATION OF McAb TO ACHIEVE 50% PLAQUE REDUCTION (μg/well) |
|---|---|
| Exp. | |
| 9B7 alone | .55 μg |
| 41C2 alone | >>100 μg |
| 9B7 + 10 μg 41C2 | .03 μg |
| Exp. 3-18-87 | |
| 26B11 alone | 6.5 μg |
| 34G7 alone | 43 μg |
| 26B11 + 10 μg 34G7 | .008 μg |
| 34G7 + 10 μg 26B11 | <.0001 μg |
| Exp. 6-8-87 | |
| 41C2 alone | >100 μg |
| 34G7 alone | 10 μg |
| 41C2 + 10 μg 34G7 | .07 μg |
| 34G7 + 10 μg 41C2 | .35 μg |

*At ≧50 g/well, neutralizing activity may reflect non-specific effect of high IgG concentration.

Group II antibody 9B7 exhibited 50% plaque reduction of HCMV Towne strain at 0.55 μg/well, whereas the simultaneous addition of 10 μg or the group I non-neutralizing antibody 41C2 resulted in >50% plaque reduction in the presence of 0.03 μg/well of 9B7. This represents a more than 10-fold increase in neutralizing activity of 9B7 and 41C2 together compared to that of 9B7 alone in the presence of complement. Moreover, binding of 9B7 to the virus in the ELISA assay was increased 2- to 4-fold in the presence of 41C2.

Neither group I mcAb 26B11 nor group II mcAb 34G7 neutralized HCMV in the presence of complement at 5 μg/well of protein. However, when increasing amounts of 26B11 were added to 10 μg of 34G7 in the presence of complement, >50% plaque reduction was observed at 0.01 μg of 26B11. Similarly, addition of as little as 0.0001 μg of 34G7 to 10 μg of 26B11 in the presence of complement resulted in >50% plaque reduction.

In a third set of experiments, various combinations of the non-neutralizating group I mcAb 41C2 and the non-neutralizing group II mcAb 34G7 were tested. 34G7 alone did not exhibit >50% plaque at 10 μg/well or protein, whereas addition of 10 μg of 41C2 together with 34G7 resulted in >50% plaque reduction at 0.35 μg of 34G7, a more than 20-fold increase in neutralizing activity. When 10 μg/well of 34G7, which was shown to be a suboptimal amount of this monoclonal to exhibit neutralizing activity, was added to varying levels of the non-neutralizing monoclonal 41C2, ≧50% plaque reduction was observed with as little as 0.07 μg/well of 41C2. Thus, the combination of two non-neutralizing antibodies may result in significant neutralizing activity.

E. Results of Detection of HCMV in Tissue Culture by Cytopathic Effect (CPE) vs. Direct Detection of Virus in Supernatants by ELISA A total of 30 patient samples were examined simultaneously for development of cytopathic effect (CPE) in fibroblast cell cultures during a 4-week observation period, and viral protein was detected in tissue culture cell monolayer lysates by ELISA using a double antibody enzyme-linked immunosorbent assay after 5 days in culture. Twenty-one of the 30 samples were negative for HCMV by ELISA, whereas 20 of the 30 samples were negative for CPE. Nine of 30 samples were positive by ELISA; 10 of 30 samples developed CPE. Thus, there was excellent agreement between the ELISA and CPE results, with 2 false negative and 1 false positive ELISA tests out of 30 samples. The presence of HCMV in tissue culture as detected by CPE was confirmed by an indirect immunofluorescence assay using the same HCMV-specific mcAb antibody as that used for detection of HCMV in the ELISA assay described hereinabove.

Discussion

We have previously isolated and characterized a major immunogenic envelope glycoprotein complex of HCMV which is made up of at least three species of antigenically-related glycoproteins linked by disulfide bonds. These glycoproteins have molecular weights of 130,000, 93,000 and 50,000–52,000 daltons. We have generated 13 murine B-cell hybridomas producing mcAbs reactive with this glycoprotein complex and its constituent glycoproteins. The individual GCA-specific mcAbs were shown to inhibit or augment the simultaneous binding of other of the GCA-mcAbs in a manner which suggested at least 7 distinct antigenic sites in 3 separate domains expressed in close proximity on the tertiary structure of the glycoprotein complex. Of particular interest, certain of these mcAbs are shown to be reactive with neutralizing sites on the glycoprotein complex in the presence of complement, whereas others are not neutralizing when assayed singly. However, simultaneous binding of pairs of neutralizing and non-neutralizing antibodies markedly enhanced the overall neutralizing activity. In some cases, 2 non-neutralizing antibodies also exhibited significant neutralization activity in combination.

Based on all of the results disclosed in the present patent application, it appears that 7 fully characterized mcAbs recognized antigenic sites within 3 separate domains on HCMV GCA. Those monoclonals recognizing epitopes within a single domain appear to be in close physical proximity. This conclusion is based on their ability to mutually compete for binding sites, whereas those in separate domains appear to recognize more distant sites based on their ability to augment the binding of monoclonals to epitopes in different domains. (FIG. 3, Panel A) The physical relationships between epitopes in different domains as well as those within individual domains appear to depend on conformational structure rather than the primary amino acid sequence, since reduction of disulfide bonds abrogates augmentation of binding in many cases. Based on the patterns of competitive inhibition and/or augmentation of binding among the mcAbs and their ability to neutralize HCMV in the presence of complement, either alone or in combination with other mcAbs, it is believed that the epitopes recognized by these monoclonals associate with each other as part of a crypt in the peptide backbone, linked by one or more disulfide bridges (FIG. 3B). Since the physical proximity of epitopes 41C2 and 26B11 in domain I and 34G7 in domain II is altered by reduction of the disulfide bond(s), mutual augmentation of binding of monoclonals recognizing these epitopes is also eliminated by reduction. In contrast, epitope 39E11 of domain I and 9B7 and 18F9 of domain II mutually inhibit binding as a result of their close proximity on the linear structure of the peptide backbone, which is not altered by reduction.

This hypothetical model suggests that the epitope(s) on GCA responsible for neutralization is located at the base of the crypt, since monoclonals recognizing these epitopes, while not recognizing other epitopes within the same domain, neutralize HCMV in the presence of complement. It also appears that augmentation of binding of a neutralizing antibody to its epitope may increase its biological activity. Moreover, changes in conformation of so-called "non-neutralizing" epitopes brought about by simultaneous binding of two non-neutralizing antibodies may result in significant viral neutralization associated with these same epitopes.

Thus, the utility of the various aspects of this invention is supported by a topographical analysis of antigenic sites on a major immunogenic envelope glycoprotein of HCMV. Moreover, a panel of 13 mcAbs are provided in which particular combinations bind synergistically to the virus and enhance the biological activity over that of either mcAb used alone. This is of particular importance in determining the clinical utility of HCMV-specific murine mcAbs for diagnostic and therapeutic purposes, given that amounts required for any individual mcAb alone may either lack sensitivity or be required in greater quantity than that practical for commercial production.

These various mcAbs may play an important role in the development of viral diagnostic tests because different mcAbs can be used in a non-competing format. For example, one mcAb recognizing a unique epitope of a particular HCMV protein can be used to capture and concentrate the virus, whereas a second mcAb which recognizes a different, non-competing epitope of the same protein can be used for immunologic detection of the viral antigen. Moreover, two mcAbs which mutually augment the binding of the other antibody to its particular antigenic site may be used to increase the sensitivity of immunologic detection of the viral antigen. The utility of this method has been demonstrated using prototype diagnostic tests, in which nitrocellulose membranes and plastic plates have been used as the captive matrix for HCMV antigen. Using the HCMV-specific mcAbs described in this application, these prototypes can detect HCMV in nanogram amounts.

Monoclonal antibodies to HCMV may also be useful in the treatment of potentially life-threatening opportunistic HCMV infections in immunosuppressed patients. Among these patients are organ transplant patients, bone marrow transplant patients, patients with congenital or acquired immune deficiency diseases, patients on immunosuppressive drugs, and patients with congenital HCMV infection. The use of mcAbs in immunotherapy may be indicated in both prophylactic treatment of high-risk patients and specific therapy in patients with serious HCMV infections. There is recent evidence suggesting that administration of hyperimmune HCMV globulin to immunosuppressed patients prior to organ or bone marrow transplantation may possibly attenuate or prevent life-threatening HCMV infections in the post-transplant period. HCMV-specific mcAbs can be generated in large quantity at low cost, and thus represent a significant advantage over hyperimmune globulin. Therapeutic administration of HCMV hyperimmune globulin to patients with active infection may also be useful, although success in this regard has been limited to date.

Monoclonal antibodies developed in our laboratory have been shown to have high specific neutralizing activity against Towne strain HCMV in vitro. Moreover, synergistic neutralizing activity using two or more monoclonal antibodies directed against different epitopes of the same glycoprotein may allow for high therapeutic activity with relatively low quantities of mixtures of mcAbs compared to that required using individual mcAbs. Also, synergistic neutralizing activity is observed over a wide range of relative concentrations of augmenting mcAbs. This should greatly simplify the selection of a pharmaceutical unit dose that will exhibit the desired therapeutic effect in patients.

It appears that certain non-neutralizing GCA-specific mcAbs (i.e., 11B4) inhibit the binding of all other mcAbs tested thus far, including those which neutralize HCMV. Therefore, HCMV hyperimmune globulin may contain certain HCMV-specific antibodies which compete with the neutralizing antibodies and alter their biological activity, thereby potentially promoting HCMV infection. Moreover, these data suggest that murine or human HCMV-specific mcAbs to be used for immunotherapy should be selected on the basis of their ability to augment the binding and neutralizing activity of other HCMV antibodies. Equally important, it is critical to exclude those mcAbs that may inhibit the binding and/or neutralizing activity of other HCMV specific antibodies.

The HCMV monoclonal antibodies described herein are murine monoclonals. They potentially can elicit an allergic response in humans. However, it is likely that most patients with serious HCMV infections will require only one or two treatments with HCMV-specific mcAbs. Therefore, the chance of significant allergic response to the mcAb is lessened. In clinical trials using other murine mcAbs, hypersensitivity reactions have not presented a major problem. Furthermore, the FDA has already approved the use of murine OKT3 mcAb (ORTHOCLONE, Ortho Pharmaceutical Co.) for cancer treatment, indicating that murine monoclonals will be an acceptable form of therapy. The following are rationales for use of murine versus human mcAbs for human therapeutics:

1. As previously mentioned, murine monoclonals have now been released by the FDA and are considered effective treatment. The allergic reactions as a result of human-anti-mouse reactions do not appear to be a major problem.
2. The murine mcAbs of the present invention are well-characterized and exhibit the appropriate immunogenic responses. Thus, the present invention provides compositions which may be used in clinical trials.
3. Alternative methods to make human mcAbs include EBV hybridomas, human-human hybridomas and human-mouse immunoglobulin genetic chimeras. In all cases, these methods do not appear to be commercially pracitical at the present time for the following reasons:
   (a) very low frequency of stable human hybridomas,
   (b) lack of availability of human fusion systems; and
   (c) very low levels of human mcAb production in the human system compared to that of the murine system (i.e., human hybridomas produce 1-10 μg/ml; murine hybridomas produce in excess of 1 mg/ml).

The present invention provides mixtures of murine anti-HCMV GCA mcAbs for prophylactic and therapeutic treatment of patients with HCMV. It would not be practical or advisable to use human monoclonals because of the lack of stability of human hybridomas and lack of the necessary production levels for obtaining a therapeutic quantity of human mcAbs. It is becoming routine for transplant patients to receive immunoprophylaxis, both pre- and post-transplant. Current therapy with HCMV globulin/plasma lacks specificity of action and carries all the risks of blood products; furthermore, this therapy is extremely expensive. Therefore, murine monoclonals would be more effective because of their antigen specificity. They would have less potential side effects because they are not a blood product and would be much less expensive to produce.

Samples of hybridomas which produce mcAbs 9B7, 41C2 and 34G7 have been deposited with In Vitro International, Linthicum, MD, in accord with the Draft Patent and Trademark Office Deposit Policy for Biological Materials, BNA PTCJ, 32, 90 (1986).

The invention has been described with reference to various specific and preferred embodiments and techniques. However, it should be understood that many variations and modifications may be made while remaining within the spirit and scope of the invention.

What is claimed is:

1. A composition consisting essentially of a mixture of
   (a) a first monoclonal antibody which binds to a first epitope on HCMV GCA, wherein said first monoclonal antibody neutralizes HCMV infectivity in vitro in the presence of complement; and
   (b) a second monoclonal antibody which binds to a second epitope on HCMV GCA, wherein said second monoclonal antibody does not neutralize HCMV infectivity in the presence of complement; wherein the neutralizing activity of the mixture is greater than the neutralizing activity of the first monoclonal antibody.

2. The composition of claim 1 wherein the first monoclonal antibody is 9B7.

3. The composition of claim 1 wherein the second monoclonal antibody is 41C2.

4. The composition of claim 1 wherein said composition is free of a monoclonal antibody which binds to a third epitope on HCMV GCA, does not neutralize HCMV infectivity in the presence or absence of complement, and which inhibits the binding of the first antibody and the second antibody.

5. A method for the in vitro neutralization of HCMV comprising treating an amount of HCMV with an amount of the composition of claim 1 in a pharmaceutically acceptable carrier, which is effective to neutralize the infectivity of the HCMV.

6. The composition of claim 5 wherein said composition is free of a monoclonal antibody which binds to a third epitope on HCMV GCA, does not neutralize HCMV infectivity in the presence or absence of complement, and which inhibits the binding of the first antibody and the second antibody.

* * * * *

UNITED STATES PATENT AND TRADEMARK OFFICE
CERTIFICATE OF CORRECTION

PATENT NO. : 5,126,130

DATED : June 30, 1992

INVENTOR(S) : Nancy O. Lussenhop et al.

It is certified that error appears in the above-identified patent and that said Letters Patent is hereby corrected as shown below:

At columns 9 and 10, line 16, for "-21%" read --+21%--.

At column 13, line 36, for ">>" read -->--.

Signed and Sealed this

Twenty-sixth Day of April, 1994

Attest:

BRUCE LEHMAN

*Attesting Officer*     *Commissioner of Patents and Trademarks*